United States Patent [19]

Hintz et al.

[11] Patent Number: 5,246,695
[45] Date of Patent: Sep. 21, 1993

[54] USE OF ALKYLGLYCOSIDE SULFOSUCCINATES FOR THE PRODUCTION OF COSMETIC PREPARATIONS AND CLEANING AGENTS

[75] Inventors: Mathias Hintz, Schlüchtern-Hohenzell; Hans-Jürgen Köhle, Schlüchtern; Christl Möller, Steinau an der Strasse; Thomas Salomon, Bad-Soden-Salmunster-Wahlert; Joachim Weigand, Freigericht, all of Fed. Rep. of Germany

[73] Assignee: REWO Chemische Werke GmbH, Fed. Rep. of Germany

[21] Appl. No.: 861,446

[22] Filed: Apr. 1, 1992

[30] Foreign Application Priority Data

Apr. 3, 1991 [DE] Fed. Rep. of Germany ....... 4110663
Apr. 4, 1991 [DE] Fed. Rep. of Germany ....... 4110852

[51] Int. Cl.⁵ .......................... A61K 7/06; A61K 7/075
[52] U.S. Cl. ........................................ 424/70; 536/4.1; 536/6
[58] Field of Search ................... 536/4.1, 6, 18.6; 424/70

[56] References Cited

U.S. PATENT DOCUMENTS

| | | | |
|---|---|---|---|
| 3,640,998 | 2/1972 | Mansfield | 536/18.3 |
| 4,299,975 | 11/1981 | Asbeck et al. | 560/151 |
| 4,597,770 | 7/1986 | Forand | 536/18.6 |
| 4,609,478 | 9/1986 | Egan | 536/4.1 |
| 4,704,453 | 11/1987 | Lorenz et al. | 536/18.6 |
| 4,709,020 | 11/1987 | Rauscher | 536/18.6 |
| 4,806,275 | 2/1989 | Johnson | 536/4.1 |

FOREIGN PATENT DOCUMENTS

| | | |
|---|---|---|
| 0190779 | 8/1986 | European Pat. Off. . |
| 0301298 | 2/1989 | European Pat. Off. . |
| 2700072 | 7/1978 | Fed. Rep. of Germany . |
| 3336760 | 4/1984 | Fed. Rep. of Germany . |
| 2011462 | 6/1982 | United Kingdom . |

OTHER PUBLICATIONS

Otey, F. H., "The Preparation and Properties of Polyoxyethylene Methyl Glucoside Fatty Esters," *J. Am. Oil Chem. Soc.*, 38: 517–520 (Oct. 1961).

*Primary Examiner*—Thurman K. Page
*Assistant Examiner*—S. Gardner
*Attorney, Agent, or Firm*—Scully, Scott, Murphy & Presser

[57] ABSTRACT

The invention relates to alkylglycoside sulfosuccinates of the general formula (1) defined herein, useful in cosmetic preparations.

13 Claims, No Drawings

USE OF ALKYLGLYCOSIDE SULFOSUCCINATES FOR THE PRODUCTION OF COSMETIC PREPARATIONS AND CLEANING AGENTS

The invention relates to the use of alkoxylated sulfosuccinates containing ester groups and based on alkyl glycosides for the production of mild cosmetic preparations and aqueous compositions which contain these compounds.

Cosmetic preparations, in particular those which come within the area of hair and body cleaning, such as shower baths, foam baths, hair shampoos, baby shampoos, baby baths and liquid soaps, contain as cleaning components mainly anionic surfactants such as carboxylates, alkyl sulfates and alkyl ether sulfates.

These preparations should clean the skin surface, preferably only the film adhering to it, which can consist of body secretions such as perspiration and fats, flakes of skin or deposited dirt from the environment. The cleaning agents should in no case dry out the skin, irritate it or impair its natural function.

As the preparations can lead, however, during their frequent—in recent years almost daily—use to irritations of the skin, use is frequently additionally made, in order to improve the skin and eye mucosa compatibility, of so-called mild surfactants such as, for example, betaines, protein derivatives, ampholytes, alkyl ether carboxylates and sulfosuccinates.

Especially for baby care agents and baby shampoos and preparations for sensitive skin, particular value is placed on extremely low contents of substances irritating the skin and eye mucosa. The anionic surfactants conventionally used because of their excellent cleaning and foam-forming properties can be rendered substantially milder in their irritant action by means of the known mild cosurfactants, but in practice improvements, in particular in the way of eye mucosa compatibility, are still required.

In high concentrations or on their own, the mild surfactants are substantially irritation-free, but then do not have foaming and cleaning properties suitable for practical use and have unsatisfactory viscosities.

A further criterion for the usefulness of the surface-active substances is their toxicity. The toxicity lies in the surfactants themselves or products thereof formed by interaction with other constituents of the formulation.

As a result of increased environmental awareness, products are additionally required which are based on natural, renewable raw substances, have no toxicity whatsoever and can be rapidly and completely degraded in municipal sewage plants without toxic intermediates.

GB Patent 2,011,462 discloses polyalkoxylated mono- and dicarboxylates of c-methylglucosides, the only surfactant disclosed being GLUCAMATE® SSE-20 from Amerchol—a mixture of the mono- and distearates of α-methylglucoside. It is used in skin-compatible preparations for removing make-up from the eyes.

German Published Specification 3,336,760 describes mixtures of at least one oligomeric alkyl- glucoside ether containing an alkyl radical having 8-10 carbon atoms, ethoxylated methylglucoside dioleate, alkyl- or hydroxyalkyl polyglycosides containing an alkyl radical having 11-18 carbon atoms and between 3-25 glycoside units and at least one nonionic polymer from the group comprising the alkyl celluloses, polyhydroxyalkyl celluloses, poly-β-alanines and polyvinylpyrrolidone as mild hair- and body-cleaning agents.

In practice, high molecular weight compounds sometimes exhibit application problems: they are very often difficult to dissolve in water and necessitate a relatively large effort to disperse them in water; occasionally it is difficult to obtain the desired viscosity immediately or the formulations tend to be "stringy" and produce a sticky feeling on the skin. Some of these disadvantages can be due to preparation and could possibly be overcome by appropriate apparatus measures and careful monitoring of the course of the process.

The object of the present invention is to overcome these disadvantages of the prior art and to make available mild, skin-compatible cosmetic preparations, in particular those which come within the area of hair- and body-cleaning.

This object is achieved by alkoxylated sulfosuccinates containing ester groups and based on alkyl glycosides additionally used according to the invention. The invention therefore relates to the use of alkylglycoside sulfosuccinates of the general formula (1)

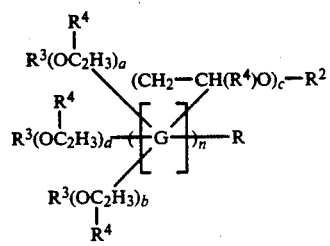

wherein each G is

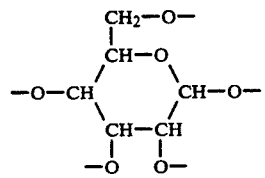

wherein R is $-(CH_2-CH(R^4)-O)_x-R^1$ wherein $R^1$ is H or a linear, saturated or unsaturated hydrocarbon radical having 1-18, preferably 1-10, in particular 1-4 carbon atoms and x is 0-10, preferably 0-5, and R is attached at the 1-position;

each $R^2$ is the same or different and is a linear, saturated or unsaturated acyl radical having 8-22 carbon atoms, preferably 12-18 or can be selected from the group consisting of natural coconut fatty acids acyl radicals carbon atoms;

each $R^3$, independently of one another, is H or the radical $[CO-CH(SO_3^-)-CH_2-COO^-]\cdot mM$, provided that $R_3$ is said radical at least once in each G;

each $R^4$, independently of one another, can be H or $CH_3$;

n is 1 to 10, preferably 1 to 6 and more preferably 1 to 3;

the sum of (a+b+d) or each unit G is 1-20, preferably 1-10, and more preferably 1-3, and c is 1-5; and each M is the same or different and is a cation of an alkali metal or an alkaline earth metal, ammonium, or H+, wherein m equals 2 divided by the valence of M; and wherein, when n is greater than 1, each G is attached to adjacent G groups at the 1,2-; 1,3-; 1,4- or 1,6-positions;

and said compounds in the production of cosmetic preparations and cleaning agents.

The invention further relates to aqueous preparations containing
A) 5-20% by weight of at least one compound according to the general formula (1) as defined above;
B) 1-5% by weight of at least one thickener;
C) 0-10% by weight of an electrolyte salt;
D) 0-10% by weight of customary auxiliaries and additives; and
E) 55-94% by weight of water.

Further embodiments of the invention are characterized by the claims.

One starting substance for the preparation of the compounds of the general formula (1) according to the invention are commercial monomers and oligomers of glucose, for example glucose syrup from Cerestar.

The degree of polymerization of the glucose varies according to the process and manufacturer and is in the range 1-10, such that n as defined above is 1-10. The compounds useful according to the invention include mixtures of compounds having these various degrees of polymerization. Although the maximum degree of polymerization n is about 10, the largest part in any composition preferably has a degree of polymerization (n) of less than 5. The mean value of n can therefore also be a decimal number, that is to say lie between two integers.

Thus, it will be recognized that the degree of polymerization n of compounds in formulations claimed according to the invention represents an average; that is, if n is defined as being in the range of 1 to 6 the composition can also comprise the comparatively small amounts of compounds in which n is greater than 6. Preferred compounds of formula (1) according to the invention have degrees of polymerization n less than or equal to 3 and in particular 1-2 with an average preferably about 1-1.5.

These glycosides are, in a first step, etherified or transetherified by generally customary processes (cf. U.S. Pat. No. 4,704,453, EP-A-0,301,298).

The group R of the glycoside is preferably an alkyl group having 1-10, preferably 1-4 carbon atoms or an alkenyl group having 2-10, preferably 2-4, carbon atoms. The group R can optionally be replaced by higher groups having up to 18 carbon atoms. R can furthermore be a polyether group of the structure —(C-$H_2$—$CH_2$—O—)$_x$—$R^1$, in which $R^1$ is H or an alkyl or alkenyl group as described above for R and x can assume values between 1-10, preferably 1-5.

In a second step the acylation reaction of one mol of fatty acid or fatty acid methyl ester or fatty acid ethyl ester respectively is carried out per glycoside unit. Instead of the fatty acids or their methyl or ethyl esters, the natural fats and oils, that is to say their glycerol esters, can also be employed.

The fatty acids used are the monobasic acids having 8-22 carbon atoms—preferably the naturally occurring acids —such as lauric acid, myristic acid, palmitic acid, stearic acid, oleic acid, linoleic acid, linolenic acid, ricinoleic acid, coconut fatty acid or their mixtures (compare J. Am. Oil Chemists' Soc. 38, 517-520 (1961) and EP-A 0,190,779). The glycoside esters are alkoxylated, preferably ethoxylated or propoxylated, by processes known per se (J. Am. Oil Chemists' Soc. 38, 517-520 (1961), U.S. Pat. No. 3,640,998). The ethoxylation or propoxylation can also be carried out before the introduction of the ester function. The amounts of ethylene oxide and/or propylene oxide are chosen to provide the desired number of alkoxy (ethoxy and propoxy) units in the molecule, as defined above. Preferably, the rate of addition is between 1 and 20 alkoxy units in total per repeating glycoside unit, values according to the invention preferably being greater than 5, in particular 8-20 alkoxy units per unit.

The reaction to give the sulfosuccinate is carried out with maleic anhydride and subsequent sulfonation with sodium sulfite according to processes known per se (compare German Published Specification 2,700,072). Reaction is carried out in this case with one mol of maleic anhydride per mol of hydroxyl group to be reacted at 60°-80° C. until the reaction is complete. The maleic acid hemiester is then added to an aqueous sodium sulfite solution (1 equivalent of sulfite per equivalent of hemiester) and sulfonated at 60°-80° C. until the sulfite has completely reacted. The aqueous product is then adjusted to neutral pH.

While commercial sulfosuccinates can only be dissolved in water in concentrations up to about 40% by weight, the compounds according to the invention surprisingly have the advantage that they can be prepared in concentrations of 50% by weight and higher as clear, low-viscosity solutions.

These compounds, which can be additionally used on their own or in a mixture, can be employed in concentrations of 5-20, preferably of 6-12% by weight, relative to the total mixture.

The number of anionic groups in the molecule is affected by the manner in which the glycoside molecules are linked to one another. If the glycoside rings are linked to one another in the 1,4- or 1,3-position, it is simpler for steric reasons to substitute all the hydroxyl groups than if the linkage is effected in the 1,6- or 1,2-position. By way of definition, and referring to the foregoing depiction of the ring structure denoted as G, the carbon atoms in the ring are numbered consecutively as 1 through 6, and the linkage through —O— which forms the ring is between the carbon atoms in positions 1 and 5.

Although theoretically 2n+1 anionic groups can be introduced into the glycoside ester, 2n to n groups are preferred according to the invention.

The mixtures according to the invention are in general aqueous compositions or aqueous alcoholic solutions, creams, emulsions or gels and can still contain the auxiliaries and additives customary in each case for adaptation to the intended application and which, apart from in aqueous cleaning agents, such as mild washing-up liquids used by hand, are in particular additionally used for the production of cosmetic preparations in the area of hair- and body-cleaning, that is to say for shower baths, foam baths, shampoos, liquid soaps, baby care agents and baby detergents.

These are foam stabilizers such as polysaccharides, carboxyvinyl polymers, polyvinylpyrrolidones, fatty acid partial glyceride polyglycol ethers, protein-fatty acid condensates; pearl luster and clouding agents such as fatty alcohols, ethylene glycol distearates, monoesters of polyhydric alcohols with higher fatty acids, polystyrene emulsions; complexing agents or sequestering agents such as salts of ethylenediaminetetraacetic acid; preservatives such as sorbic acid, citric acid, ascorbic acid, chlorhexidine, 8-hydroxyquinoline and its salts, benzalkonium chloride, dimethylalkylbenzylammonium chloride and small amounts of fragrances, colorants, skin cosmetic active substances, vegetable extracts and buffer substances.

Thickeners additionally used according to B) can according to the invention be any material which effectively thickens the formulation. Preferred thickeners include commercial fatty acid partial glyceride polyglycol ethers such as REWODERM ® LI 420, REWODERM ® LI 48 (trademark of REWO Chemische Werke GmbH, Steinau an der Straße) in amounts from 1 to 10, preferably from 2 to 4% by weight, relative to the total mixture.

Suitable electrolyte salts are all alkali metal, alkaline earth metal and ammonium salts which are soluble at 20° C. in amounts of at least 1% by weight. Those preferred are sodium chloride, magnesium chloride and ammonium chloride, which can be additionally employed in amounts up to about 10% by weight, preferably 1–5% by weight, relative to the total formulation.

The content of wash-active substance (B-WAS) given in the following examples is titrated by the customary two-phase titration with benzalkonium chloride against Methylene Blue as indicator (cf. S. R. Epton, Nature (London), 160, 1967, p. 795).

The hydrolysis number is a measure of the free and bound acids contained in fats and technical fatty acids. It gives the number of milligrams of potassium hydroxide which are necessary to hydrolyze 1 gram of substance or technical fatty acids (mg of KOH/g). The values are determined by the standard methods of the German Society for Fat Chemistry (DGF): DGF C-V3.

The hydroxyl value is used to determine the content of hydroxyl groups and gives the number of milligrams of potassium hydroxide which are necessary to neutralize the acetic acid consumed by 1 gram of substance during the acetylation (mg of KOH/g) The values are determined by the DGF standard method DGF C-V17A.

The solids content is determined by drying to constant weight at 105° C.

Preparation of the compounds according to the invention

Example 1

Preparation of butylglucoside coconut fatty acid ester 8 g of $K_2CO_3$ was added to 826 g (3.5 mol) of n-butylglucoside and the reaction mixture was heated to 120° C. 750 g of coconut methyl ester was added dropwise to the reaction mixture at 50 mbar over the course of 2 h and was then reacted for 4 h at 120° C. and 30 mbar. The resulting methanol was immediately removed by distillation during the course of this. A yellow, highly viscous material having the following analytical data resulted:

| Hydrolysis value | 110 mg of KOH/g |
|---|---|
| Hydroxyl value | 430 mg of KOH/g |

Example 2

Preparation of the polyethylene oxide ether 463 g of (1.05 mol) of butylglucoside ester from Example 1 were treated with 2.3 g of KOH and treated in portions with 464 g (10.5 mol) of ethylene oxide at 120° C. in an autoclave so that the pressure was at most 5 bar. A highly viscous yellow material having the following analytical values resulted:

| Hydrolysis value | 54 mg of KOH/g |
|---|---|
| Hydroxyl value | 223 mg of KOH/g |

Example 3 Preparation of the sulfosuccinate 258 g (0.3 mol) of butylglucoside ester ethoxylate from Example 2 was stirred with 57.6 g (0.6 mol) of maleic annydride at 70° C. for 2 h. The maleic acid hemiester was then added to a solution of 350 g of water at 60° C. containing 74.1 g (0.6 mol) of $Na_2SO_3$ and stirred at this temperature until the $SO_2$ content of the solution was <0.01%. A clear solution having a 48.3% solids content and 43.5% Benzavlon washactive substance (B-WAS) resulted.

The following examples were carried out following Examples 1–3.

Example 4

258 g (0.3 mol) of butylglucoside ester ethoxylate from Example 2 was reacted as described in Example 3 with 29 g (0.3 mol) of maleic anhydride and then sulfonated in a solution of 300 g of water containing 37 g (0.3 mol) of $Na_2SO_3$. The solution had a solids content of 49% and a B-WAS of 41%.

Example 5

258 g (0.3 mol) of butylglucoside ester ethoxylate from Example 2 was reacted as described in Example 3 with 87 g (0.9 mol) of maleic anhydride and then sulfonated with a solution of 400 g of water containing 111 g (0.9 mol) of $Na_2SO_3$. The solution had a solids content of 47% and a B-WAS of 43%.

Example 6

200 g (0.3 g mol) of butylglucoside ester ethoxylate (prepared as in example 2, except that the mole ratio of ethylene oxide:ester was 5:1) was reacted with 59 g (0.6 mol) of maleic anhydride at 80° C. As described in Example 1, the hemiester was then sulfonated in a solution of 330 g of water and 77 g (0.61 mol) of $Na_2SO_3$. The sulfosuccinate had 49% solids and a B-WAS of 41%.

Example 7

200 g (0.3 mol) of the butylglucoside ester ethoxylate as described in Example 6 was reacted with 88.5 g (0.9 mol) of maleic anhydride at 80° C. Analogously to Example 3, the sulfonation was carried out in 400 g of water and 116 g of $Na_2SO_3$. The sulfosuccinate had 50% solids and a B-WAS of 44%.

Example 8

200 g (0.3 mol) of butylglucoside ester ethoxylate as in Example 6 was reacted with 29.5 g (0.3 mol) of maleic anhydride at 75° C. Analogously to Example 3, sulfonation was carried out in 270 g of water containing 38 g (0.3 mol) of Na$_2$SO$_3$. The sulfosuccinate had 48.2% solids together with 28.1% B-WAS.

Example 9

220 g (0.5 mol) of butylglucoside ester from Example 1 was reacted analogously to Example 3 with 49 g (0.5 mol) of maleic anhydride and then sulfonated in 500 g of water containing 63 g (0.5 mol) of Na$_2$SO$_3$. The sulfosuccinate had 38.3% solids and a B-WAS of 23.2%.

Example 10

238 g (1 mol) of butylglucoside was treated with 0.5 g of potassium hydroxide and treated in portions with 440 g (10 mol) of ethylene oxide at 140° C. in an autoclave so that the maximum pressure did not exceed 5 bar. A viscous, yellow product having a hydroxyl value of 360 resulted.

Example 11

678 g (1 mol) of the product from Example 10 was treated with 3 g of K$_2$CO$_3$ and heated to 120° C. under an N$_2$ atmosphere. Under a vacuum of 100 mbar, 210 g (0.95 mol) of coconut methyl ester was added dropwise to the reaction solution over the course of about 2 h and the mixture was then reacted for a further 4 h at 120° C. The resulting methanol was continuously removed from the system. A pale-yellow, viscous material having the following analytical values resulted:

| Hydrolysis value | 60 |
|---|---|
| Hydroxyl value | 240 |

Example 12

890 g (1 mol) of butylglucoside ethoxylate ester from Example 11 was reacted as described in Example 3 with 98 g (1 mol) of maleic anhydride and then sulfonated with a solution of 1100 g of water and 126 g of Na$_2$SO$_3$. A pale solution having a solids content of 49% and a B-WAS of 31% resulted.

TABLE 1

| Example | R | R$^2$ | R$^3$ | R$^4$ | Σ | d | n |
|---|---|---|---|---|---|---|---|
| 1* | n-butyl | coconut acyl | 3 × H | H | 0 | 0 | about 1.3 |
| 2* | n-butyl | coconut acyl | 3 × H | H | 10 | 0 | about 1.3 |
| 3 | n-butyl | coconut acyl | 1 × H, 2 × sulfosuccinate | H | 10 | 0 | about 1.3 |
| 4 | n-butyl | coconut acyl | 2 × H, 1 × sulfosuccinate | H | 10 | 0 | about 1.3 |
| 5 | n-butyl | coconut acyl | 3 × sulfosuccinate | H | 10 | 0 | about 1.3 |
| 6 | n-butyl | coconut acyl | 1 × H, 2 × sulfosuccinate | H | 5 | 0 | about 1.3 |
| 7 | n-butyl | coconut acyl | 3 × sulfosuccinate | H | 5 | 0 | about 1.3 |
| 8 | n-butyl | coconut acyl | 2 × H, 1 × sulfosuccinate | H | 5 | 0 | about 1.3 |
| 9 | n-butyl | coconut acyl | 2 × H, 1 × sulfosuccinate | H | 0 | 0 | about 1.3 |
| 10* | n-butyl | H | 3 × H | H | 10 | about 1-3 | about 1.3 |
| 11* | n-butyl | coconut acyl | 3 × H | H | 10 | about 1-3 | about 1.3 |
| 12 | n-butyl | coconut acyl | 2 × H, 1 × sulfosuccinate | H | 10 | about 1-3 | about 1.3 |

Coconut acyl = mixture of natural C$_{12-16}$ fatty acids
* = Precursor materials
Sulfosuccinate = —CO—CH(SO$_3$—)—CH$_2$—COO—2 Na$^+$ or —CO—CH$_2$—CH—(SO$_3$—)—COO—2 Na$^+$
Σ = the sum of (a + b + c + d)

All formulations are given in percent by weight calculated relative to solids.

The following surfactants, when referred to herein, are referred to by terminology employed according to the Cosmetic, Toiletry and Fragrance Association (CTFA).

| Reference Number in Formulation | Compound Name |
|---|---|
| 1) | Disodium laureth sulfosuccinate |
| 2) | Sodium laureth sulfate |
| 3) | Cocoamidopropyl betaine |
| 4) | PEG-80 glyceryl tallowate |
| 5) | Glyceryl stearate |
| 6) | PEG-200 glyceryl tallowate mod. |
| 7) | Disodium cocoamphodiacetate |

| Basic formulation: hair shampoo | | |
|---|---|---|
| Example 4 or 12 | 2-6 | parts by weight |
| REWOPOL ® NL 3-28 | 6-15 | " |
| REWODERM ® LI S 75$^{6)}$ | 1-3 | " |
| demin. water | to 100 | |

| Basic formulation: baby shampoo or shampoo for sensitive skin | | |
|---|---|---|
| Example 4 or 12 | 3-8 | parts by weight |
| REWOTERIC ® AM 2 C NM$^{7)}$ | 2-10 | " |
| REWOTERIC ® AM B 13 H$^{3)}$ | 4-8 | " |
| REWODERM ® LI 48-50$^{4)}$ | 1-4 | " |
| demin. water | to 100 | |

| Basic formulation: cream | | |
|---|---|---|
| Example 4 or 12 | 1-5 | parts by weight |
| Glycerol monodistearate | 2-10 | " |
| Cetyl alcohol | 1-4 | " |
| Paraffin oil 3.5° E | 4-12 | " |
| Glycerol | 1-5 | " |
| demin. water | to 100 | |
| Preservative | as required | |

| Basic formulation: shower bath | | |
|---|---|---|
| Example 4 or 12 | 2-10 | parts by weight |
| REWOTERIC ® AM B 13 | 2-8 | " |
| REWOPOL ® NL 3-28 | 5-15 | " |
| REWODERM ® LI 48-50 | 1-4 | " |
| demin. water | to 100 | |

| Basic formulation: washing-up liquid | | |
|---|---|---|
| Example 12 | 1-5 | parts by weight |
| REWOPOL ® NL 3-28 | 1-30 | " |
| REWOTERIC ® AM CAS | 1-5 | " |
| REWOPOL ® LA 6 | 1-10 | " |
| demin. water | to 100 | |

Application check

Shower bath

The glycoside derivatives developed have been assessed in the test recipe by a test panel of 20 persons (female and male) with respect to
foaming power, foam structure
feeling of the wet skin
feeling of the dried skin
for skin compatibility (zein values) compare: Z. Götte "Hautverträglichkeit von Tensiden, gemessen am Lösevermögen für Aein" (skin compatibility of surfactants, measured by dissolving power for zein) Chem. Phys. Appl. Surface Active Subst. Proc. Int. Congr. 4 (1964) 83-90.

Assessment scheme: <200 mg of N/100 ml = non-irritating
200–400 mg of N/100 ml = slightly irritating
>400 mg of N/100 ml = irritating

Plate washing test

1. Principle

The number of artificially soiled plates which can be cleaned in a washing-up liquid solution until the liquor is exhausted is determined.

2. Production of the test soiling 2.0 parts by weight of technical oleic acid, 49.9 parts by weight of wheatmeal flour and 0.1 part by weight of the dye Sudan Red are successively stirred into a melt of 48.0 parts by weight of lard at 50° C. and homogenized.

3. Coating the plate

The plates are first washed, rinsed with clear water and additionally rinsed with isopropanol. 2 g of the test soiling at 40° C. are then uniformly distributed on each dried plate on the inner surface using a brush and then stored for 24 h at 20° C. and 65% relative atmospheric humidity.

4 Preparation of the washing liquors

Washing liquor A 8 l of tap water at 50° C. having a German hardness (° dH) of 10° and a content of the test substance to be checked of 0.02% by weight (relative to solids) is placed in a bowl and stirred for 2 min with a blade stirrer at 300 rpm in such a way that sufficient foam results.

Washing liquor B 10 l of cold tap water (20° C. 10° dH) which is continuously replaced by running fresh water (5 l/min) are placed in a second bowl.

5. Washing process

The soiled plates are washed in succession for 30 seconds each under the surface of the washing liquor A using the washing brush. They are then rinsed by simple immersion in liquor B. Washing is carried out until liquor A is exhausted. This is recognized by the disappearance of the foam, the visually recognizable remaining of soil particles on the washed plates or the floating of black or red fat particles on the surface of the liquor A.

6. Assessment

The number of plates washed perfectly clean is determined by subjective assessment of at least 3 persons. The following are stated:

| Number of plates | as stated |
|---|---|
| Concentration of the washing liquor in g/l | 0.02% solids content |
| Water hardness in mmol of $Ca^{++}$/l | 10°dH |
| Washing temperature in °C. | 50 |

| Shower Bath Formulation | 1 | 2 | 3 |
|---|---|---|---|
| Example 4 | 5 | — | — |
| Example 12 | — | 5 | — |
| REWOTERIC ® AM B 13[3] | 3 | 3 | 3 |
| REWOPOL ® NL 3-28[2] | 11 | 11 | 16 |
| REWODERM ® LI 48-50[4] | 2 | 2 | 2 |
| demin. water | to 100 | to 100 | to 100 |
| pH adjusted with citric acid to | 6.5 | 6.5 | 6.5 |
| Foaming power[4] | good foam development | good foam development | good foam development |
| Foam structure[4] | creamy - soft | creamy - soft | having large bubbles |
| Feeling - wet skin[4] | creamy - soft | creamy - soft | soft |
| Feeling - dry skin[4] | smooth - soft | smooth - soft | slightly dry |

[4] The assessment was carried out by a graded assessment system, where the above mentioned assessment represents the arithmetic mean.

| Skin Cleaning Preparation, Reduction of Zein Values | 1 | 2 | 3 | 4 |
|---|---|---|---|---|
| Example 4 | 4.5 | — | — | — |
| Example 12 | — | 4.5 | — | — |
| REWOPOL ® SB FA 30[1] | — | — | 4.5 | — |
| REWOPOL ® NL 3-28[2] | 10.5 | 10.5 | 10.5 | 15 |
| demin. water | 85 | 85 | 85 | 85 |
| pH adjusted with citric acid to | 6.5 | 6.5 | 65 | 6.5 |
| Assessment of the foam quality | creamy having minute bubbles | creamy having minute bubbles | having minute bubbles | having large bubbles |
| Feeling after washing on the dry skin | smooth, soft | smooth, soft | soft | somewhat rough |
| Zein values | 120 mg of N/100 ml | 122 mg of N/100 ml | 270 mg of N/100 ml | 300 mg of N/100 ml |

Hair shampoo

The glycoside derivatives developed have been assessed in the recipe by 10 volunteers experienced in application for:
Combability
Volume of the hair and hold of the hairstyle

| | Formulation | | |
|---|---|---|---|
| | 1 | 2 | 3 |
| Example 4 | 4.5 | — | — |
| Example 12 | — | 4.5 | — |
| REWOPOL ® NL 3-28[2] | 10.5 | 10.5 | 15 |
| REWODERM ® LI S 75[6] | 2 | 2 | 2 |
| demin. water | 83 | 83 | 83 |
| pH adjusted with citric acid to | 6.5 | 6.5 | 6.5 |
| Combability | 5 | 6 | 2 |
| Volume of the hair | 6 | 5 | 3 |
| Hold of the hairstyle | | | |

| Assessment of combability: | |
|---|---|
| 1-3 | Difficult to comb through: the hair offers considerable resistance to the combing process |
| 4-7 | The hair can be combed through relatively easily, combing resistance is decreased, adequate for a conditioning shampoo depending on the hair type |

-continued

| | |
|---|---|
| 8-10 | Reserved for the subsequent aftertreatment by so-called hair-rinse agents |

Assessment of the hair volume and of the hold of the hairstyle

| | |
|---|---|
| 1-3 | The hair is dry or dull and lifeless; poor hold of the hairstyle |
| 4-7 | The hair is soft and bouffant at the same time together with a good hold of the hairstyle |
| 8-10 | The hair is soft and smooth, but too loose, as a result the hairstyle does not hold well. |

The assessment was carried out by a graded point system, where the abovementioned assessment represents the arithmetic mean.

Skin cream

Use of aqueous sulfosuccinates based on glycoside as emulsifiers in O/W emulsions

| HLB value | Example 4 | about 16 |
|---|---|---|
| | Example 12 | about 16 |

Determination according to W. C. Griffin ("Calculation of Surface Active Agents by HLB", Journal Soc. Cosm. Chem. 1, 311 (1949)).

| Skin Cream O/W Test Formulation | 1 | 2 | 3 | 4 |
|---|---|---|---|---|
| Example 4 | 2 | — | — | — |
| Example 12 | — | 2 | — | — |
| Stearyl alcohol +3EO | — | — | 2 | — |
| REWOMUL ® MG[5] | 6 | 6 | 6 | 6 |
| REWOPOL ® SB FA 30[1] | — | — | — | 2 |
| Cetyl alcohol | 2 | 2 | 2 | 2 |
| Liquid paraffin 3.5° E | 8 | 8 | 8 | 8 |
| Glycerol | 3 | 3 | 3 | 3 |
| Preservative | as required | as required | as required | as required |
| demin. water | to 100 | to 100 | to 100 | to 100 |
| Stability of the emulsion at 50° C., 20° C. and 40° C. | stable | stable | stable | instable |
| Appearance | smooth white cream | smooth white cream | smooth white cream | greasy, emulsion breaks |

Assessment of the properties on the skin by 10 volunteers; more than 80% assessed the stable test recipes 1 and 2
- as easy to spread on the skin
- as easily absorbed into the skin
- the skin is smooth and soft, without becoming sticky and greasy. The comparison recipe No. 4 is not assessed the same and is furthermore unstable.

| Baby shampoo or hair and body shampoo for sensitive skin | | | |
|---|---|---|---|
| | Formulation | | |
| | 1 | 2 | 3 |
| Example 4 | 6 | — | — |
| Example 12 | — | 6 | — |
| REWOTERIC ® AM 2C NM[7] | 6 | 6 | 6 |
| REWOTERIC ® AM B 13[3] | 4 | 4 | 4 |
| REWODERM ® LI 48-50[4] | 2 | 2 | 2 |
| REWOPOL ® NL 3-28[2] | — | — | 6 |
| demin. water | to 100 | to 100 | to 100 |

-continued

| Baby shampoo or hair and body shampoo for sensitive skin | | | |
|---|---|---|---|
| | Formulation | | |
| | 1 | 2 | 3 |
| pH adjusted with citric acid to | 6.5 | 6.5 | 6.5 |
| Zein values, mg of N/100 ml | <70 | <70 | about 150 |
| Skin roughness according to Padberg[B] | slight roughening | slight roughening | distinct roughening |

[B]Testing of skin compatibility according to Padberg, J. Soc. Cosm. Chem. 20, 719-728 (1969)

The formulation shown is a "non-irritating" washing solution only "slightly roughening" the skin. The assessment "slightly roughening" is the lowest which can be obtained with surfactants by the method shown.

Assessment of skin roughness according to Padberg:
Grade 1 very slight roughening—does not differ from the blank area
Grade 2 slight roughening—% Padberg below 50
Grade 3 distinct roughening—% Padberg over 50
Grade 4 heavy roughening—does not differ significantly from the sodium lauryl sulfate area (comparison substance)

| Test Formulation: Skin-compatible washing-up agents for manual use | | | | |
|---|---|---|---|---|
| | Formulation | | | |
| | 1 | 2 | 3 | 4 |
| Example 12 | — | 3 | 1.5 | — |
| REWOPOL ® NL 3-28[7] | 18 | 18 | 18 | 18 |
| REWOTERIC ® AM CAS[3] | 1.5 | — | 1.5 | — |
| REWOPOL ® LA 6[4] | 1.5 | — | — | 3 |
| Water | to 100 | to 100 | to 100 | to 100 |
| Plate washing test Number of plates | 12 | 20 | 18 | 12 |
| Zein values (skin compatibility) | 220 | 195 | 220 | 250 |
| Foam height (mm) + 0.5 ml of | 195/185 | 190/180 | 195/190 | 190/180 |
| Olive oil + 1.0 ml of | 190/180 | 190/180 | 195/185 | 190/180 |
| Olive oil | 190/185 | 190/180 | 190/180 | 190/180 |

What is claimed is:

1. An alkylglycoside sulfosuccinate of the formula (1)

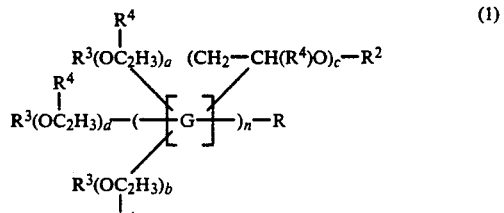

(1)

wherein each G is

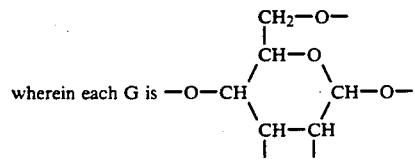

-continued $$\text{wherein R is } -(CH_2-\underset{\underset{R^4}{|}}{CH}-O)_x-R^1$$

wherein $R^1$ is H or a linear, saturated or unsaturated hydrocarbon radical having 1-18 carbon atoms and x is 0-10 and R is attached at the 1-position;

$R^2$, and when n is greater than 1 each $R^2$, is independently a linear, saturated or unsaturated acyl radical having 8-22 carbon atoms;

$R^3$, and when n is greater than 1 each $R^3$, is independently H or the radical $[CO-CH(SO_3^-)-CH_2-COO^{31}]\cdot mM$, provided that $R^3$ is said radical at least once in each G;

$R^4$, and when n is greater than 1 each $R^4$, is independently H or $CH_3$;

n is 1 to 10 the sum of (a+b+d) in each unit G is 1-20 and c is 1-5; and

M, and when n is greater than 1 each M, is independently a cation of an alkali metal or an alkaline earth metal, ammonium, or $H^+$, wherein m equals 2 divided by the valence of M; and wherein, when n is greater than 1, each G is attached to adjacent G groups at the 1,2-; 1,3-; 1,4- or 1,6- positions.

2. An alkylglycoside sulfosuccinate as claimed in claim 1, wherein

R is an alkyl radical having 1-4 carbon atoms; $R^2$, and when n is greater than 1 each $R^2$, is an acyl radical selected from the group consisting of natural coconut fatty acid acyl radicals; and n is 1-2.

3. A compound as claimed in claim 1 wherein when n is greater than 1 each G group is connected to an adjacent G group at the 1,4-position.

4. An alkylglycoside sulfosuccinate as claimed in claim 1 wherein $R^1$ is H or a linear, saturated or unsaturated hydrocarbon radical having 1-10 carbon atoms.

5. An alkylglycoside sulfosuccinate as claimed in claim 4 wherein $R^1$ has 1-4 carbon atoms.

6. An alkylglycoside sulfosuccinate as claimed in claim 1 wherein x is 0-5.

7. An alkylglycoside sulfosuccinate as claimed in claim 1 wherein $R_2$ is a linear, saturated or unsaturated acyl radical having 12-18 carbon atoms.

8. An alkylglycoside sulfosuccinate as claimed in claim 1 wherein n is 1 to 6.

9. An alkylglycoside sulfosuccinate as claimed in claim 8 wherein n is 1 to 3.

10. An alkylglycoside sulfosuccinate as claimed in claim 1 wherein the sum of (a+b+c) on each G unit is 1-10.

11. An alkylglycoside sulfosuccinate as claimed in claim 10 wherein the sum of (a+b+c) on each G unit is 1-3.

12. A compound as claimed in claim 1 wherein $R^1$ is H or a linear saturated os unsaturated hydrocarbon radical having 1-10 carbon atoms, x is 0-5; $R^2$ is a linear, saturated or unsaturated acyl radical having 12-18 carbon atoms; n is 1 to 6; and the sum of (a+b+c) on each unit G is 1-10.

13. A compound as claimed in claim 4 wherein $R^1$ is H or a linear, saturated or unsaturated hydrocarbon having from 1-4 carbon atoms; n is 1 to 3; and the sum of (a+b+c) on each unit G is 1-3.

* * * * *

UNITED STATES PATENT AND TRADEMARK OFFICE
CERTIFICATE OF CORRECTION

PATENT NO. : 5,246,695
DATED : September 21, 1993
INVENTOR(S) : Mathias Hintz, et al.

It is certified that error appears in the above-indentified patent and that said Letters Patent is hereby corrected as shown below:

Column 1, lines 55-56: "mon-oand" should read --mono-and--

Column 1, line 56: "c-" should read -- α - --

Column 2, line 54: after "12-18" insert --carbon atoms--

Column 2, line 56: delete --carbon atoms--

Column 5, line 43: after "KOH/g)" insert --.--

Column 8, line 65: "Aein" should read --Zein--

Column 9, line 31: "4" should read --4.--

Column 13, line 15, Claim 1: "COO$^{31}$" should read --COO$^-$--

Signed and Sealed this

Thirteenth Day of September, 1994

Attest:

BRUCE LEHMAN

Attesting Officer    Commissioner of Patents and Trademarks